| United States Patent [19] | | [11] | 4,166,744 |
|---|---|---|---|
| Smith | | [45] | Sep. 4, 1979 |

[54] ADHESIVE CEMENTS ESPECIALLY ADAPTED TO SURGICAL USE

[76] Inventor: David F. Smith, 2840 N. Ocean Blvd., Ste. 709, Ft. Lauderdale, Fla. 33308

[21] Appl. No.: 801,609

[22] Filed: May 31, 1977

Related U.S. Application Data

[63] Continuation-in-part of Ser. No. 593,885, Jul. 7, 1975, Pat. No. 4,046,578.

[51] Int. Cl.² ............................................... C09K 3/00
[52] U.S. Cl. .................................. 106/35; 260/998.11
[58] Field of Search .......................................... 106/35

[56] References Cited

U.S. PATENT DOCUMENTS

| 3,509,089 | 4/1970 | Dougherty | 106/35 |
|---|---|---|---|
| 3,655,605 | 4/1972 | Smith et al. | 106/35 |
| 3,856,737 | 12/1974 | Foster et al. | 106/35 |
| 4,046,578 | 9/1977 | Smith | 106/35 |

*Primary Examiner*—Theodore Morris

[57] ABSTRACT

Zinc oxide and weak unpolymerized and polymerized acids when mixed in the presence of water form adhesives that quickly set to firm, hard cements that are especially useful in dentistry and surgery. Mixtures of ZnO and solid such acids can be provided but must be exceptionally dry and be so maintained in order to have satisfactory shelf life.

23 Claims, No Drawings

ADHESIVE CEMENTS ESPECIALLY ADAPTED TO SURGICAL USE

In my copending patent application, Ser. No. 593,885, filed July 7, 1975, (U.S. Pat. No. 4,046,578) of which this application is a continuation-in-part, I have disclosed ZnO powder and finely-divided solid, weak, unpolymerized, polycarboxy acids in which the particles of the mixture are bonded together by agents that do not largely interfere with subsequent rapid wetting with water, to become adhesive and to rapidly set to strong, hard cements. Also these acids in aqueous solution are disclosed therein, separated from the bonded ZnO.

Polymerizeable, unsaturated acids are in general more expensive to produce in solid form without turning to very slowly-soluble, glassy solids and thus are not provided in solid form where the other, cheaper acids can be used. However when they offer sufficient advantage, they can be made in the form of solid powder through treatment of moderately concentrated solutions of them by (1) freeze-drying (2) drying rapidly in thin films on heated drums and (3) precipitation by adding non-solvents that are water-miscible, such as acetone, methylethyl ketone and the lower aliphatic alcohols. Polymethacrylic acid is, however, exceptional among such polymer acids, as will be shown herein.

While still useful in bonding together metals, textiles, paper, wood and plastic materials, the present invention cements are particularly designed for medical use, for example as (1) a base or lining in a tooth cavity (2) a temporary fixing for the bands of orthodontic appliances (3) for sealing root-canals (4) in certain instances for permanent fillings and (5) in orthopedics to assist in replacing bone fragments. In dental usage it is not generally required that the solid particles be bonded together in the ingredients of the cement-forming materials and the ZnO may be provided as a free-flowing powder and the acid separately as an aqueous solution of 10 to 70% by weight. The ZnO and aqueous acid may be supplied, for example, both in a plastic container or capsule of flexible, transparent film with the aqueous acid in a separate enclosed capsule or within a partition that may be pierced to let acid into powder and mix at the point of use—the acid being of the correct concentration and amount to react with the enclosed powder, thus forming a single dosage amount of cement, or they may be provided in individual containers. However, there is considerable advantage even in dental use, in providing a bonded ZnO in the form of thin sheets. This permits of accurately gaging the amount of ZnO taken for a single usage, by the area of sheet taken, instead of the common practice of using a pencil-shaped dispenser with semi-spherical cavities at its ends which the operator fills with powder as a gage of the amount of ZnO to use. It is awkward to fill and level-off the cavity and pack the powdered ZnO uniformly and shake out the powder sticking to the cavity walls so as to end up with even a roughly accurate amount of powder. With the sheet of bonded ZnO powder, lines or cross-hatching can be provided on the hard-surfaced mixing-pad used, in order to show the proper area of sheet; and the corresponding proper amount of liquid acid is well gaged by dispensing it through a dropping spout.

When water-resistant cements are required using the unpolymerized acids herein disclosed, an excess of 10% or more of ZnO must be used and thus it is necessary to accurately gage the proportions of ZnO and acid by a convenient means such as above described. With the herein-disclosed polymer acids, satisfactory water-resistance and strength of the cements is achieved with a much wider range of proportions, although even here optimum results require accurate control of proportions.

While mixtures of ZnO powder and aqueous polyacrylic acid have been disclosed in cement, I find that polymethacrylic acid offers important advantages. Due to its relative insolubility in water it can be produced relatively easily in dry, solid form; but when wet in water it has the reaction of a weak acid and reacts with ZnO. A mixture of dry ZnO and dry polymethacrylic acid can thus be wet in water and rapid reaction can be had using active ZnO without the need for providing time for mixing and without encountering the use of viscous solutions as are normally required for achieving the best cement strengths which require avoidance of excess water in the ingredients of the cement. With the polymethacrylic acid, only enough water need be present to obtain a moldable mix, or only enough to moisten the mix and cause it to react. Thus a bonded sheet needs only to be wet with water and it is used without essential deformation of its shape.

The unpolymerized acids disclosed in my parent application are weak, organic, unpolymerized (monomer) polycarboxylic acids that are rapidly wet and considerably soluble in water; including citric, carboxylated cellulose, malonic and malic. The polymer acids herein disclosed, in addition to polyacrylic and polymethacrylic, are unsaturated alpha-beta-dicarboxylic acids including polymaleic, polyfumaric, polyitaconic acids and copolymers of the latter 3 acids with each other and with less than 10 mol percent unsaturated monocarboxylic acids. The separately enclosed aqueous acids are at concentrations from 10 to 70by weight depending upon the solubility of each, with in each case only enough water beyond the solubility requirement to form a workable mix with the ZnO or to control the setting-time. The polymer acids may have a molecular-weight from 5,000 to 150,000 as determined from the equation: specific viscosity equals $1.05 \times 10^{-3}$ $(mw)0.54$ where mw is the viscosity-determined molecular-weight.

The ZnO may contain up to 20% of its weight (preferably 10%) of powdered MgO, $Bi_2O_3$, $Ca_3(PO_4)_2$ or $CaF_2$. It may otherwise contain up to 100% of its weight of colloidal silica or glass powder and it is useful to have up to 20% $CaF_2$ in view of the known penetration of fluoride ion into calcerous structures and its decay-resistant properties therein. Such penetration also appears to strengthen the bond between cement and such structures.

In orthopedic use it is usually desirable to have my cement-forming materials in the form of thin bands or sheets or strips which I provide by my herein-described bonding methods. The sheets are then used by wetting in aqueous acid, or in water when they contain the solid acid as described, the excess aqueous acid or water being stripped off the surface when not supplied in proper dosage form. Such strips or bands can then be applied across fracture-lines or around them. When supplied in the strips containing mixed, ultra-dry ZnO and solid acid, mere application to moist tissue surfaces will provide enough water to set the materials in the strips.

My cements show strong adherence to calcerous structures like teeth and bones and the ZnO-citric acid type cements in particular show strong adherence to the skin; they thus become especially useful in dentistry and surgery and they are not unacceptable or irritating in use.

When used as more or less permanent fillings or linings in dentistry, the unpolymerized polycarboxy acids should contain at least 10% excess ZnO over its chemical equivalent of acid; but naturally very large excess reduces strength and workability; with the polymer acids normal usage often has involved larger excess many times because of lowering of the viscosity of the cement mix due to excess water needed in the viscous polymer-acid solutions used. The high molecular-weight polymer acids give higher strength cements but when ZnO and polymer acid are supplied separately the correspondingly high viscosity polymer solutions make mixing with the ZnO difficult. Thus my dry mix of acid and ZnO offer great advantage in that excess water is not needed and strength of the cement is improved thereby and, since time for mixing need not be provided, very active ZnO with correspondingly fast setting can be achieved.

Mixtures of ZnO and solid acid of whatever type must be exceptionally well dried (I call them ultra-dry) and especially well protected from atmospheric moisture in order to remain unreacted in storage for appreciable lengths of time. Thus ordinary 5-mil thick polyethylene film is totally inadequate and one must package, for example, in thick polyethylene or polypropylene film, polyethylidene chloride (Saran) film or metal foil or glass containers.

EXAMPLE I

Solid polymethacrylic acid was thoroughly dried by distilling of the fine-ground mixture of it with benzene. 3 grams of this were mixed with 10 grams of ZnO that had been mixed with a water dispersion of polyvinyl acetate (pvoac) containing 0.2 g. solid pvoac of softening-point 100° C. and the mixture thoroughly dried in a vacuum oven at 80° C. The dried polymethacrylic acid and the dried ZnO with its discontinuous sprinkling of pvoac particles, were then made into a thick paste with anhydrous isopropyl alcohol, the paste spread out evenly on a glass plate and dried up to 100° C. in a vacuum oven to evaporate the alcohol and leave a thin sheet about 1 mm. thick bonded by discrete particles of pvoac that had been softened by the heating but not melted so as to cover a large part of the surface of the solid ZnO and acid. Part of this strip when moistened in water became adhesive and quickly set to a strong, hard cement. The remainder of the sheet was sealed in aluminum foil laminated on the inside with a thin film of plastic. This part of the sheet still maintained its ability to become adhesive and set quickly to a hard cement when wet in water, even after many weeks.

EXAMPLE II

Solid polymaleic acid was obtained by freeze-drying its aqueous solution. It was ball-milled and dried by distilling benzene from a mixture with it. 3 g. of the dry solid was mixed with 8 g. of active ZnO after thorough drying. The mix was made into a thick paste with anhydrous isopropanol containing 0.2 g. dried dextran of a type that softens in the alcohol and wets but does not dissolve in water. The paste was spread out and dried as in Example I to similarly yield a thin, well bonded sheet. Part of the sheet was wet in water and it yielded an adhesive mass that quickly set to a hard, firm cement. The remainder of the sheet was packaged as in Ex. I and aged similarly.

EXAMPLE III 34 g. anhydrous citric acid was mixed with 26 g. dry, active ZnO and 1 g. dry zein (corn protein) and a paste of the mix made in anhydrous methanol containing 25% by volume of carbon tetrachloride. A portion of the paste was spread out on a glass plate and dried as before in a vacuum oven at 80° C. to form a dry, bonded film which tested satisfactorily as in Ex. II.

EXAMPLE IV 12 g. of ZnO powder was heated for several hours at 1200° C. in order to deactivate it. (Alternatively a ZnO powder was used that had a thin coating of lauric acid.) 10 g. of this powder made into a thick paste with water containing 0.2 g. purified, "acid" casein and 1 g. $NH_3$ was thoroughly dried in a vacuum oven at 80° C. after being spread out to form a dry, well-bonded sheet. When a portion of this sheet was wet with a 50% aqueous solution of polyacrylic acid of 25,000 mw, it wet through and formed an adhesive mass that set in a few minutes to form a firm, hard cement.

EXAMPLE V 10 g. of dry ZnO was mixed with 3 g. of dry polymaleic acid. The mixture was made into a thick paste with anhydrous isopropanol containing 0.2 g. of a dispersion of polyvinyl acetate of softening-temperature 100° C., the dispersion being made by adding a solution of the pvoac in the methyl ether of ethylene glycol to the isopropanol during active stirring. A portion of the paste was spread on a glass plate and thoroughly dried at 100° C. in a vacuum oven to give a well-bonded thin sheet. This sheet wet quickly in water, became adhesive and quickly set to a hard, strong cement.

EXAMPLE VI 10 g. of the ZnO of Ex. IV was made into a thick paste with water containing 0.25 g. of pvoac as a dispersion, the pvoac having a softening temperature of 100° C. The paste was spread on a glass plate and dried in a vacuum oven at 100° C. to form a well-bonded, thin sheet. A 2 g. portion of this dried sheet wet through quickly with 5.2 g. of a 50% aqueous solution of citric acid. The sheet became adhesive and rapidly set to give a hard, strong, water-resistant cement after about 5 minutes.

When additional tensile strength is required in the strips of cement, for example, if used across a bone fracture-line to hold the fragments together, strong, fine filaments may be embedded in the strip in the required direction as it is made so that as the cement forms they will be firmly held in the strip. It may usually be desirable that such filaments be absorbable and non-irritating in living tissues in which case they would be of polyglycolic acid such as are used for absorbable surgical sutures. In thin strips the filaments would be of size 00 to 5-0 as designated in sutures. If a bonded strip of my cement might be used to cover and hold in approximation the edges of a surface wound or incision, surgical gauze or other inert textile material can be embedded in the strip as it is made and such a reinforced strip could, for example be wound around a broken finger, arm or leg and set in place—and if the strip is of considerable length, it can be provided in the form of a convolutely-wound roll like a bandage-roll. The invention cements, especially the ZnO-citric acid cements are particularly adhesive to the skin as they form.

Normally when used in dentistry my products do not need to be sterile—only "clean"—but if used in and around a wound, they would be provided sterile and packaged by known methods to maintain sterility in storage and permit of removal for use without destroying their sterility. For example, when a bonded strip of dry ZnO and dry acid is provided, it could be in the conventional "sterile pack" comprising, a double paper envelope sterilized by ethylene oxide or by high-energy electron discharge, or heat-sterilized in double envelopes of either paper, high-melting plastic or metal foil. By "double envelopes," of course is meant one envelope containing the product, the one envelope being then enclosed in an outer envelope. Then, at the point of use, the outer envelope is removed and discarded without contaminating the inner envelope. The sterile ZnO-dry acid mix from the inner envelope is then wet with sterile water to activate the mix. With solutions where heat-sterilization is not appropriate, sterilization of the packaged material can be by high-energy electron discharge or a few drops of propylene oxide can be added inside the package, which sterilizes the contents after which the propylene oxide hydrates to form propylene glycol or otherwise decomposes.

In general my products should be free of toxic, irritating or allergenic materials. Commercial ZnO made by either the "American" or "French" process is very pure and very finely-divided. The bonding agents herein disclosed are used in amounts from about 0.5% to 2% of the weight of the solid powders to be bonded. As mentioned, when unpolymerized acids are used, the production of water-resistant cements requires at least a 10% excess of ZnO over the chemical equivalent of acid used. At the expense of loss of strength, up to about 200% excess may be used with slowing of the setting-time. With the polymer acids, an amount of acid (solid basis) from about 12% to 60% of the weight of ZnO has been used with good strength cements resulting; the tendency being for better strength with higher mw polymer acid. In the prior art where the ZnO mix with solid polymer acid has not been disclosed, the time of mixing for ZnO and acid solution, the high viscosity of solutions of high concentration and high molecular-weight has greatly restricted the use of high mw acid and high solution concentration. Thus the present invention permits use of high nw acid and use of only enough water to wet through my mix of solid acid and ZnO and consequently avoids the water accompanying more dilute solutions and the mixing problem with high viscosity solutions; the tendency being toward higher cement strengths with less water present and with use of higher mw polymer acid. As pointed out, with my mixes of dry ZnO and dry polymer acid (particularly dry polymethacrylic that is relatively easily prepared) only enough water needs be used to wet through the mix at most, and polymer acids up to 250,000 mw can be used without the limitations of prior art practice. The polymer acids will at least be wettable in water but do not need to be greatly soluble.

While I have indicated the use of bonding agents in amount from about 0.5% of the weight of powder to be bonded, I may use up to 5% in order to slow down the setting, in addition to the delay of the set by high-temperature heating of the ZnO and by coating the surface of the ZnO with a hydrophobic material in order to slow its wetting, which is easily done by coating with, for example, propionic acid or lauric acid whereby the acid radical reacts with the ZnO leaving the hydrophobic (non-polar) radical of the organic acid exposed and, when needed, this type of coating may be used to 5%. Since a very active ZnO can react with acid very rapidly, ability to slow the set is important since a very fast set gives rise to an increase of temperature that may be uncomfortable and/or damaging to the tissues. Thus I slow the set by these devices singly or in combination, and I may point out that increasing the proportion of binder in my bonded products, even using a water-wettable binder, let alone a non-wettable binder like my pvoac, will slow the wetting of the cement-forming ingredients and thus slow the set. This undesirable rise in temperature has not been adequately controlled in the prior art where the cements have mostly been used upon relatively insensitive areas of the teeth.

While generally I have disclosed use of the polymer acids in the proportion of from 12% to 60% of the weight of the ZnO (and this has been the prior art practice due to the viscosity and mixing limitations above mentioned) my disclosures permit their use from about 12% of the weight of the ZnO up to an amount corresponding to 110% of their chemical equivalent in ZnO; and in the case of the unpolymerized acids, from 110% to 20% of their chemical equivalent of ZnO; in every case with the requirement to use enough to wet through the ZnO and to yield a moldable product before setting.

With further respect to my use of bonding-agents, it should be pointed out that the agent must become at least slightly adhesive during the bonding procedure. This means, in the case of polyvinyl acetate used in water dispersion or dispersion in any medium in which it is insoluble, it must be at least slightly softened in the mix in order to bind the particles of the mix, which normally means that it must have a softening-temperature at the temperature at which the mix is dried or the solvent evaporated from it. Otherwise a small proportion of a pvoac solvent must be in the slurry, taking care not to cover all of the mix with a water-repellant coating. In the case of agents that are water-wettable, they are applied in solution, at least softened and can completely cover the particles of the mix without completely preventing wetting.

I wish to particularly emphasize the method I may use to sterilize my products, by enclosing within the package in contact with the cement-forming materials a few drops of propylene oxide. When the package is closed it permeates the interior and sterilizes product and package. Thus, using the double-envelope sterile pack, a few drops of the propylene oxide would be put into the inside of each of the two envelopes, after which the envelopes would be sealed. Upon standing sterilization is accomplished and excess oxide either hydrates to the glycol or otherwise reacts with the materials present or decomposes, leaving no oxide to cause irritation in use, at least after about 2 week's standing at about room temperature.

My use of thin, bonded sheets of ZnO makes possible another useful procedure which avoids the limitations of the prior art imposed by the difficulty and time involved in attempting to mix viscous solutions with ZnO powders. My procedure is to spread over the surface of the thin sheet the viscous solution so that it wets through the thin sheet and wipe off the excess solution if required. Otherwise I may provide a corresponding sheet of inert, impervious material such as filled paper or plastic whose surface is wet with sufficient viscous solution so that it may be contacted with the ZnO sheet in order to wet through it. In order to facilitate such wetting-through of the ZnO sheet, I may include either in the ZnO sheet or the other sheet or both, a wetting-agent such as a cationic like Na lauryl sulfate, sodium alkyl naphthyl sulfonate, dioctyl Na sulfosuccinate, Na octylphenoxy-ethoxy ether sulfonate or triethanol amine lauryl sulfate; an anionic like beta-phenoxyethyl-docecyl ammonium bromide or other quaternary ammonium salt or a non-ionic like alkyl phenyl ethers of polyethylene glycol. Such wetting-agents are used in a proportion of from a few tenths of 1 percent up to about 1% of the materials involved.

Having thus described my invention, what I claim is:

1. The method of making a mix of ultra dry powdered ZnO and an ultra dry powdered weak organic solid acid, which mix when moistened with water quickly becomes adhesive and then quickly sets to a strong hard cement; selecting the said ZnO from the class consisting of (a) essentially pure ZnO and (b) ZnO treated with about 0.5% of its weight of propionic acid and (c) ZnO treated with about 0.5% of its weight of lauric acid; and selecting the said acid from the class consisting of (A) at least one powdered solid unpolymerized polycarboxylic acid that is quickly wet by and considerably soluble in water; (B) at least one solid powdered polymer acid that is quickly wet by and considerably soluble in water; mixing said selected ZnO and said selected acid in an inert volatile anhydrous liquid in amount at least sufficient to thoroughly wet the powder surface to form a slurry; evaporating the said liquid from said slurry after forming the slurry into a desired form while the slurry still retains at least a portion of the liquid; and protecting the said slurry and dried product from moisture until use.

2. The method of claim 1 wherein to said slurry is added with vigorous stirring a bonding agent in amount from 0.5 to 5% of the weight of solids, selected from the class consisting of (1) a dispersion of a volatile anhydrous liquid of water-insoluble polyvinyl acetate of a softening-temperature within the range at which the said liquid is evaporated, said temperature being at least a few degrees above maximum room temperature (2) casein when the said liquid is such as to cause it to be at least slightly adhesive before said liquid is completely evaporated (3) dextran of a type that is relatively water-insoluble but wettable in water and the said liquid is such as to cause it to be at least slightly adhesive before said liquid is completely evaporated and (4) zein when said liquid is such as to cause it to be at least slightly adhesive before said liquid is completely evaporated.

3. The method of claim 1 wherein the said powdered ZnO is bonded and formed into a thin sheet, the said weak acid is selected from the class consisting of (1) a bonded thin sheet and (2) a concentrated aqueous solution separated from the said thin sheet of ZnO.

4. The method of claim 1 wherein the said liquid is selected from the class consisting of (1) anhydrous methanol (2) anhydrous propanol (3) anhydrous isopropanol (4) anhydrous ethanol (5) anhydrous acetone (6) mixtures of anhydrous methanol and carbon tetrachloride and (7) compatible mixtures of the foregoing liquids.

5. The method of claim 1 wherein up to 20% of the weight of powder is mixed with a powdered solid selected from the class consisting of MgO, $Bi_2O_3$, $Ca_3(PO_4)_2$, colloidal silica and $CaF_2$.

6. The method of claim 1 wherein to the slurry is added up to 1% of the weight of solids of a wetting-agent in order to permit of wetting the mix quickly throughout with a minimum of moisture.

7. The method of claim 1 wherein the said unpolymerized acid is selected from the class consisting of citric acid, malonic acid and malic acid.

8. The method of claim 1 wherein the said polymer acid is selected from at least one of the class consisting of polyacrylic, polymethacrylic, unsaturated alpha-, beta-dicarboxylic acids including polymaleic, polyfumaric, polyitaconic acids and copolymers of the latter 3 acids with each other and with up to 10 mol % of unsaturated monocarboxylic acids.

9. The method of claim 1 wherein the said powders are sterilized and packaged so as to maintain sterility during storage and as used.

10. The method of claim 9 wherein the said powders are sterilized by enclosing within each package a minor amount of propylene oxide of an amount not in excess of that which will leave no undecomposed residue after about 2 weeks' standing at room temperature.

11. The method of claim 1 wherein parallel reinforcing strands are embedded within said part.

12. The method of claim 1 wherein inert textile reinforcing material is embedded within said part.

13. The method of claim 11 wherein the said reinforced part is formed into a long, narrow strip and wound convolutely in a roll.

14. The method of claim 12 wherein the said reinforced part is formed into a long, narrow strip and wound convolutely in a roll.

15. The method of claim 1 wherein the said ZnO is heated to a high temperature sufficient to decrease its reactivity.

16. The method of claim 11 wherein the said strands are of tissue-resorbent polyglycolic acid of diameter 2-0 to 5-0 in the nomenclature used for surgical sutures.

17. The method of claim 9 wherein the sterility is maintained by packaging in the conventional, double-enveloped sterile-pack.

18. Claim 1 wherein there is provided a package having 2 compartments when the said parts are required to be kept separate in storage, comprising an outer enclosure of flexible material containing a flexible barrier on one side of which is disposed one of said parts and on the other side the second part, with means for breaking said barrier at the time of use to permit mixing of the 2 parts within the said outer enclosure, at least one of said enclosure and barrier materials being selected as needed from the class consisting of moisture-impermeable material, plastic material and transparent material.

19. Claim 1 wherein the relative amounts of said parts are made such as to provide single dosage units for a specified use.

20. Claim 1 wherein the said ZnO part is in the form of a thin sheet which is to be wet through by a second part at the time of use and the said second part is small in amount relative to the amount of the part containing the ZnO; the said second part is disposed as a thin coating uniformly spread over and adhering to the surface of an impermeable backing sheet of the same lateral shape and area as of the said thin sheet containing the ZnO, so that the coated surface of the second sheet may be pressed over the first sheet in order to wet through the sheet containing the ZnO.

21. Claim 1, in parts which comprise ZnO and acid, packaging separate from said part containing a mix of water and the acid part with an amount of water from that just sufficient to wet through the ZnO part up to an amount equal to 4 times the weight of dry acid, the thin sheet of the ZnO part being sufficiently thin to be rapidly wet through by the herein-said water-acid mix and the said mix being small enough in amount so that no more than about sufficient to wet through and form a cement.

22. The method of claim 1 which includes a part in the form of a thin sheet and a separate part with which it is to be mixed at the point of use, in fixed proportion to said separate sheet, a combination including an impervious mixing sheet cross-hatched with lines to enable gaging the amount of it to be used, and a container with a dropping spout holding the said separate part when it is a liquid so that the said liquid may be gaged in amount by the number of drops used.

23. The method of preparing the said solid polymer acid of claim 1, by a procedure selected from the class consisting of (1) freeze-drying a solution thereof (2) rapidly drying a solution thereof in a thin film on heated drums and (3) precipitating said acid by adding to its aqueous solution a non-solvent of said acid that is water miscible.

* * * * *